(12) United States Patent
Romano

(10) Patent No.: US 9,965,852 B2
(45) Date of Patent: May 8, 2018

(54) SYSTEM AND METHOD FOR EVALUATING ANISOTROPIC VISCOELASTIC PROPERTIES OF FIBROUS STRUCTURES

(71) Applicant: Anthony J. Romano, Washington, DC (US)

(72) Inventor: Anthony J. Romano, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 206 days.

(21) Appl. No.: 14/250,606

(22) Filed: Apr. 11, 2014

(65) Prior Publication Data

US 2014/0316245 A1 Oct. 23, 2014

Related U.S. Application Data

(60) Provisional application No. 61/813,219, filed on Apr. 18, 2013.

(51) Int. Cl.
*G06T 7/00* (2017.01)
*A61B 5/055* (2006.01)
*A61B 5/00* (2006.01)

(52) U.S. Cl.
CPC ............. *G06T 7/0012* (2013.01); *A61B 5/055* (2013.01); *A61B 5/4064* (2013.01); *A61B 5/4519* (2013.01); *A61B 5/725* (2013.01); *A61B 5/7253* (2013.01); *A61B 5/4082* (2013.01); *G06T 2207/10088* (2013.01); *G06T 2207/10092* (2013.01); *G06T 2207/30016* (2013.01)

(58) Field of Classification Search
CPC .............................. A61B 5/055; G06T 7/0012
USPC .......................... 600/410, 411; 382/128–132
See application file for complete search history.

(56) References Cited

U.S. PATENT DOCUMENTS

| 2004/0075659 | A1 | 4/2004 | Taubin |
| 2009/0007674 | A1 | 1/2009 | Kwon et al. |

(Continued)

OTHER PUBLICATIONS

Romano AJ, Scheel M, Hirsch S, Braun J, Sack I. Investigation of the Anisotropic Properties of White Matter Tracts in the Human Brain using Waveguide Constrained MR Elastography. In: Proceedings of the 19th Scientific Meeting of the International Society for Magnetic Resonance in Medicine, Montreal, Canada, May 2011. p. 1480.*

(Continued)

*Primary Examiner* — Amelie R Gillman
*Assistant Examiner* — Carolyn Pehlke
(74) *Attorney, Agent, or Firm* — US Naval Research Laboratory; William P. Ladd

(57) ABSTRACT

System and method for diagnosing brain conditions including evaluating fiber pathways of white matter tracts using a diffusion tensor imaging (DTI) process, tracking the propagation of waves traveling at specific angles to the fiber pathways by performing a 3D magnetic resonance elastography (MRE) process at the same spatial resolution and voxel position as the DTI, analyzing the viscoelastic properties using an inversion having at least nine elastic coefficients, determining the curvature along the pathways, differentiating the spatial-spectral filter twice with respect to arc length along the pathways, and diagnosing a brain condition based on the viscoelastic properties.

20 Claims, 7 Drawing Sheets

(56) References Cited

U.S. PATENT DOCUMENTS

2011/0178390 A1    7/2011   Li
2012/0215101 A1    8/2012   Maleke et al.
2012/0268128 A1   10/2012   Lake et al.

OTHER PUBLICATIONS

Romano, A. J., et al. "Determination and analysis of guided wave propagation using magnetic resonance elastography." Magnetic resonance in medicine 54.4 (2005): 893-900.*
Papazoglou, Sebastian, et al. "Multifrequency inversion in magnetic resonance elastography." Physics in medicine and biology 57.8 (2012): 2329.*
Polyanin (Laplace Equation, http://eqworld.ipmnet.ru/en/solutions/lpde/lpde301.pdf, May 25, 2005).*
Kriz (Microstructure Lectures, http://www.jwave.vt.edu/crcd/kriz/lectures/Anisotropy.html, Jun. 26, 2002).*
Oliphant, Travis E., et al. "Complex-valued stiffness reconstruction for magnetic resonance elastography by algebraic inversion of the differential equation." Magnetic resonance in Medicine 45.2 (2001): 299-310.*
Fisher et al. (Frequency Filter, http://homepages.inf.ed.ac.uk/rbf/HIPR2/freqfilt.htm, Jul. 2, 2004).*
Romano, Anthony, et al. "In vivo waveguide elastography of white matter tracts in the human brain." Magnetic resonance in medicine 68.5 (2012): 1410-1422 (online publication date: Jan. 17, 2012).*
Physics Hypertextbook (http://physics.info/kinematics-calculus/, Sep. 8, 2010).*
Baird, Christopher S. "Helmholtz decomposition of vector fields." University of Massachusetts Lowell (2012).*
International Preliminary Report on Patentability and Written Opinion of the International Searching Authority for PCT/US2014/034451, dated Oct. 20, 2015, 8 pages.

* cited by examiner

11

$$\begin{bmatrix} C_{11} & C_{12} & C_{13} & 0 & 0 & 0 \\ C_{12} & C_{22} & C_{23} & 0 & 0 & 0 \\ C_{13} & C_{23} & C_{33} & 0 & 0 & 0 \\ 0 & 0 & 0 & C_{44} & 0 & 0 \\ 0 & 0 & 0 & 0 & C_{55} & 0 \\ 0 & 0 & 0 & 0 & 0 & C_{66} \end{bmatrix}$$

FIG. 3

SYSTEM AND METHOD FOR EVALUATING ANISOTROPIC VISCOELASTIC PROPERTIES OF FIBROUS STRUCTURES

CROSS-REFERENCE TO RELATED APPLICATIONS

This Application is a non-provisional application claiming priority to provisional application 61/813,219 filed on Apr. 18, 2013, entitled METHODOLOGY AND ALGORITHM FOR THE EVALUATION OF THE MATERIAL MODELS AND ELASTIC COEFFICIENTS OF ANISTROPIC MEDIA under 35 USC 119(e). The entire disclosure of the provisional application is incorporated herein by reference.

BACKGROUND

Methods and systems disclosed herein relate generally to noninvasive methods to evaluate the anisotropic properties of fibrous structures such as neuronal pathways in the human brain (white matter) and muscle for diagnostic purposes.

It is known that the material parameters (such as stiffness and viscosity) of human tissue are affected by injury and disease. For example, the stiffness of both gray and white matter decreases in patients with Amyotrophic Lateral Sclerosis (ALS), Multiple Sclerosis (MS), and Alzheimer's Disease (AD). Similarly, in patients with muscular degeneration and myocardial infarction, there are distinct differences in the fiber architecture and stiffness. Therefore, it is of interest to provide a methodology for the noninvasive evaluation and diagnosis of these conditions that improve upon current techniques.

Previously-developed methods to noninvasively evaluate the material parameters of human tissue typically use knowledge of elastic displacements provided by a single measurement modality (such as Ultrasound (US) or Magnetic Resonance Elastography (MRE)) and an isotropic Helmholtz inversion algorithm. Romano, A., et al., *Evaluation of a Material Parameter Extraction Algorithm using MRI-Based Displacement Measurements, IEEE Transactions on Ultrasonics, Ferroelectrics, and Frequency control*, 2000; 47: 1575-1581; and Oliphant, T. et al., *Complex-valued Stiffness Reconstruction for Magnetic Resonance Elastography by Algebraic Inversion of the Differential Equation, Magnetic Resonance in Medicine*, 2001; 45: 299-310.

These are reasonable approaches for media which are isotropic (meaning that the material stiffness constants are the same in every direction and are represented by two elastic coefficients, one longitudinal and one shear). However, if the medium is comprised of fibers such as muscle and white matter pathways, it is considered to be anisotropic, meaning that waves propagate within these structures as if they were waveguides and the material stiffness constants depend upon the symmetry of the fibrous structures and elastic wave velocities depend on the direction of wave propagation through them. Within media such as these, the material constants can number from three to twenty-one, requiring more sophisticated inversion methods for their evaluation. In addition to knowledge of the elastic displacements in three dimensions, these latter methods require knowledge of the orientation of these waveguides in space as well as appropriate anisotropic inversion algorithms which are lacking in currently available approaches.

Waveguide Elastography (WGE) combines diffusion tensor imaging (DTI), MRE, spatial-spectral filtering, a Helmholtz decomposition, and inversions for the assessment of the anisotropic elastic constants of fibrous structures, and was demonstrated in the Corticospinal Tracts (CSTs) of five healthy human volunteers (Romano, A., et al., *In Vivo Waveguide Elastography of White Matter Tracts in the Human Brain, Magnetic Resonance in Medicine*, 2012; 68: 1410-1422.). Specifically, DTI was used to evaluate the fiber pathways of the CSTs which have been observed to act as waveguides for externally induced wave propagation. 3D-vector field MRE was performed at the same spatial resolution and voxel position achieved by DTI in order to track the propagation of waves traveling at specific angles to the fiber directions. Using this waveguide methodology, the viscoelastic properties of the CSTs were analyzed using an orthotropic material model comprised of nine independent elastic constants. Redundancies in the solutions for the orthotropic coefficients indicated that the CSTs could be well represented by hexagonal anisotropy (transverse isotropy) comprised of five independent elastic constants.

The previously described method was also applied to a cohort of 28 volunteers, 14 of which had been diagnosed with ALS and 14 of which were healthy, age matched controls (Romano, A., et al., *In Vivo Waveguide Elastography: Effects of Neurodegeneration in Patients with Amyotrophic Lateral Sclerosis, Magnetic Resonance in Medicine*, 2013; DOI 10.1002/mrm.25067). ALS is a rapidly progressive neurodegenerative disease affecting the upper and lower motor neuron with an average life expectancy of only about 2-3 years after symptom onset. The diagnosis of ALS is currently based largely on clinical signs. Both upper and lower motor neuron involvement have to be present to confirm the diagnosis. However, especially the assessment of upper motor neuron involvement can be difficult from clinical signs alone. Hence, there is an ongoing search for reliable biomarkers in ALS. Currently, neuroimaging is performed to rule out any pathologies that could mimic ALS symptoms. Conventional MRI is, in the majority of patients, unremarkable especially at an early stage of the disease. Certain imaging signs/features, e.g. a T2-hyperintensity of the CST or a signal reduction in the primary motor cortex can sometimes be observed in ALS patients, but these signs are neither very sensitive nor specific for ALS. More advanced methods, e.g. Magnetization Transfer Imaging (MTI) and metrics derived from Diffusion Tensor Imaging (DTI) (such as fractional anisotropy (FA), parallel diffusivity (PD), mean diffusivity (MD), and radial diffusivity (RD)) are evaluated as biomarkers for the detection of upper motor neuron involvement and show promising results.

What is needed, however, is a system that evaluates appropriate dynamic models and associated viscoelastic constants in arbitrarily curved anisotropic biological media. In this latter study, when compared to healthy controls, it was found that the stiffness of the CSTs of the patients with ALS was significantly reduced due to neurodegeneration of the myelin sheaths.

SUMMARY

The system and method of the present embodiment provide a noninvasive method to evaluate the anisotropic viscoelastic properties of fibrous structures such as neuronal pathways in the human brain (white matter) and muscle using sound for diagnostic purposes. Specific applications include the diagnosis of various neurological conditions such as ALS, MS, AD, and Traumatic Brain Injury (TBI), as well as various diseases in muscle such as degeneration and myocardial infarction in the heart. This detection is enabled through the evaluation of the appropriate anisotropic models and corresponding material coefficients such that they may be used as metrics for correlation with pathology.

The system and method of the present embodiment are based on the fusion of two FDA approved clinical measurement modalities (i.e. MRE and DTI) and an adaptive anisotropic inversion algorithm (described in Romano, A. et al., *In Vivo Waveguide Elastography of White Matter Tracts in the Human Brain*, Magnetic Resonance in Medicine 68 (5): pp. 1410-1422 (2012)). MRE uses a phase contrast Magnetic Resonance Imaging (MRI) approach for the noninvasive measurement of intentionally induced dynamic elastic displacements throughout biologic media, while DTI uses multi-aspect magnetic fields measured with MRI for the determination of water perfusion along pathways such as muscle and nerve fibers. By using these two data streams along with computing Laplacians as inputs to an anisotropic inversion algorithm, the dynamic models and associated viscoelastic material parameters of the media along the pathways can be evaluated, alleviating ambiguity in the inversion process within complex biological media. The stiffness values and the velocities (which are the square root of the stiffness values divided by the density) are the outputs of the system and method of the present embodiment.

The system and method of the present embodiment can provide a clinically relevant evaluation of complex, unknown biological media within minutes, noninvasively, and is not based on the use of harmful X-ray measurement techniques such as computed tomography (CT). The system and method of the present embodiment can also detect ALS, while a typical isotropic Helmholtz inversion method cannot. The system and method of the present embodiment can evaluate orthotropic myocardial muscle stiffness and orthotropic properties of other white matter structures, in vivo. Further, the system and method of the present embodiment can analytically evaluate a generalized non-linear expression for the calculation of the Laplacians which can accurately include the effects of curvature of the waveguides. Still further, the system and method of the present embodiment can perform spatial-spectral filtering procedures that can provide a global band-limited filter prior to the application of the local spatial-spectral filter which reduces noise and improves the inversion results. Even still further, the system and method of the present embodiment can include sliding window band-limited filters that shift as a function of the central or principal wavenumbers for each frequency based upon spectral analysis along the waveguides prior to inversion. The system and method of the present embodiment can calculate a rotating reference frame based on a point-normal form representation of the plane perpendicular to the principal DTI vectors along the waveguides, which can alleviate ambiguity inherent in standard rotating Frenet reference frame methods. The system and method of the present embodiment can include an automated tractography algorithm that evaluates the nearest neighbor family of vectors for pathway continuation to be used in the evaluation of the Laplacians. In the system and method of the present embodiment, the current anisotropic inversion models (currently orthotropic and lower) can be extended to include monoclinic (thirteen elastic coefficients) and triclinic (twenty-one elastic coefficients) to accommodate more complicated fibrous structures. The analytical evaluation of a generalized non-linear expression for the calculation of the Laplacians can more accurately include the effects of curvature of the waveguides. The spatial-spectral filtering procedures which first perform a global band-limited filter prior to the application of the local spatial-spectral filter can reduce noise and improve the inversion results.

BRIEF DESCRIPTION OF THE DRAWINGS

FIG. 3 is an orthotropic stiffness tensor showing its nine independent coefficients;

DETAILED DESCRIPTION

Figure 1:
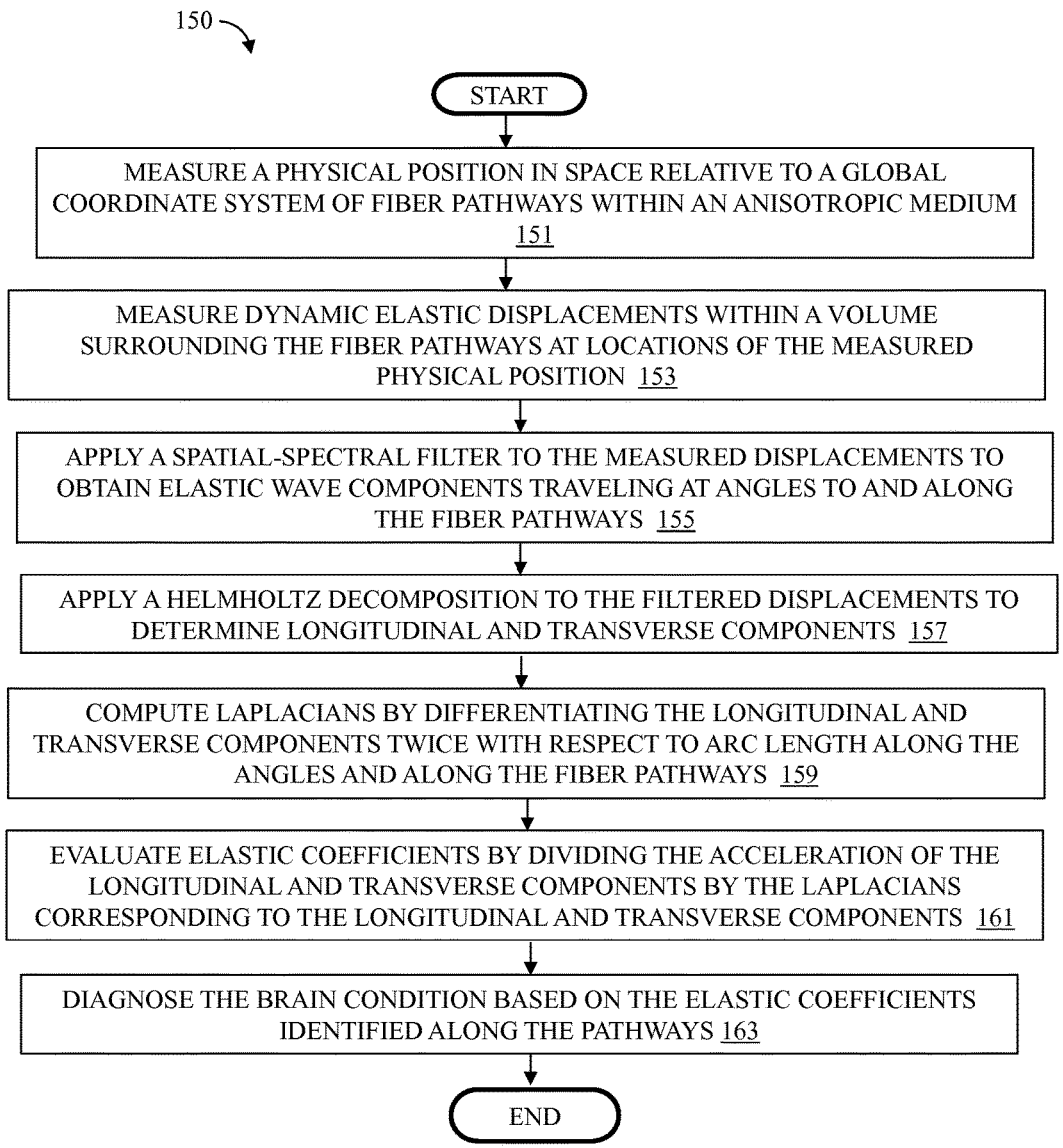
FIG. 1 is a flowchart of the method of the present embodiment.

The problems set forth above as well as further and other problems are solved by the present teachings. These solutions and other advantages are achieved by the various embodiments of the teachings described herein below. Referring now to FIG. 1, method 150 for diagnosing a brain condition can include, but is not limited to including, measuring 151 a physical position in space relative to a global coordinate system of fiber pathways within an anisotropic medium, measuring 153 dynamic elastic displacements within a volume surrounding the fiber pathways at locations of the measured physical position, applying 155 a spatial-spectral filter to the measured displacements to obtain elastic wave components traveling at angles to and along the fiber pathways, applying 157 a Helmholtz decomposition to the filtered displacements to determine longitudinal and transverse components, 159 computing Laplacians by differentiating the longitudinal and transverse components twice with respect to arc length along the angles and along the fiber pathways, 161 evaluating elastic coefficients by dividing the acceleration of the longitudinal and transverse components by the Laplacians corresponding to the longitudinal and transverse components, and diagnosing 163 the brain condition based on the elastic coefficients identified along the pathways. In another embodiment, a noninvasive computer-based method for diagnosis of brain conditions can include, but is not limited to including, determining fiber pathways of white matter tracts using a diffusion tensor imaging (DTI) process, the white matter tracts having viscoelastic properties, the DTI process having a specific spatial resolution and a voxel position, measuring the elastic waves traveling within a volume surrounding the fiber pathways by performing a 3D magnetic resonance elastography (MRE) process at the same spatial resolution and voxel position as the DTI, identifying the elastic waves traveling at pre-selected angles with respect to the white matter tracts using a spatial-spectral filter on the measured elastic waves, evaluating longitudinal and transverse components of the identified elastic waves using a Helmholtz decomposition, evaluating Laplacians of the identified elastic waves by differentiating the longitudinal and transverse components twice with respect to arc length, dividing the acceleration of the longitudinal and transverse components by the Laplacians corresponding to the longitudinal and transverse components to obtain viscoelastic coefficients, and diagnosing the brain conditions based on the viscoelastic coefficients.

Method 150 can optionally include applying a global band-limited filter before applying the spatial-spectral filter, applying a sliding window band-limited filter based on the longitudinal and transverse components, calculating a local reference frame based on the global coordinate system and on a plane perpendicular to the pathways, and extending the pathways using automated tractography. The inversion can be an orthotropic inversion, a monoclinic inversion, or a triclinic inversion.

MRE uses a phase contrast Magnetic Resonance Imaging (MRI) approach for the noninvasive measurement of intentionally induced dynamic elastic displacements throughout biological media. The MRE measurements can be performed on, for example, but not limited to, a standard 1.5 T clinical MRI scanner manufactured by SIEMENS®, München, Germany. For the displacement measurements using MRE, a head-cradle extended-piston driver can be used for monochromatic excitation in the range from 50-200 Hz. A piezoelectric actuator can also be used to excite the human head as well. A single-shot spin-echo Echo Planar Imaging (EPI) sequence can be used for rapid 3D motion field acquisition capable of acquiring a full set of MRE data typically within less than three minutes per volunteer per frequency consisting of 128×112×70 pixels with a 2×2×2 $mm^3$ isotropic voxel resolution. The three directions of the encoding gradient can provide the phase and the three Cartesian components of the displacement field at two (or more) equally spaced time steps over one vibration period. The motion encoding gradients can be matched to the frequency of mechanical vibration and include two periods of a cosine approximated by a trapezoidal shape providing the first moment nulling. Further imaging parameters can include echo time (TE), 99 ms, and repetition time (TR), 7210 ms.

DTI uses multi-aspect magnetic fields measured with MRI for the determination of water perfusion along pathways such as nerve fibers and muscle. DTI can provide a set of orthogonal unit vectors describing the orientation of the local reference frame of the waveguide. The DTI measurements can evaluate the fiber positions of the CSTs using, for example, a single-shot EPI sequence (TR/TE-8500/96 ms) with 12 non-collinear directions and one $B_0$ volume (b–value=1000 $s/mm^2$, six averages). The spatial resolution and image slice positions can be identical to those of the MRE measurements. Tensor calculation and tractography along the CSTs can be performed using the tools from, for example, the FMRIB Software Library (FSL), specifically dtifit and probtrackx. For the fiber position measurements using DTI, a single-shot EPI sequence, for example, can be used with twelve noncollinear directions and six averages. Spatial resolution and image slice positions can be the same as in MRE.

Figure 2:
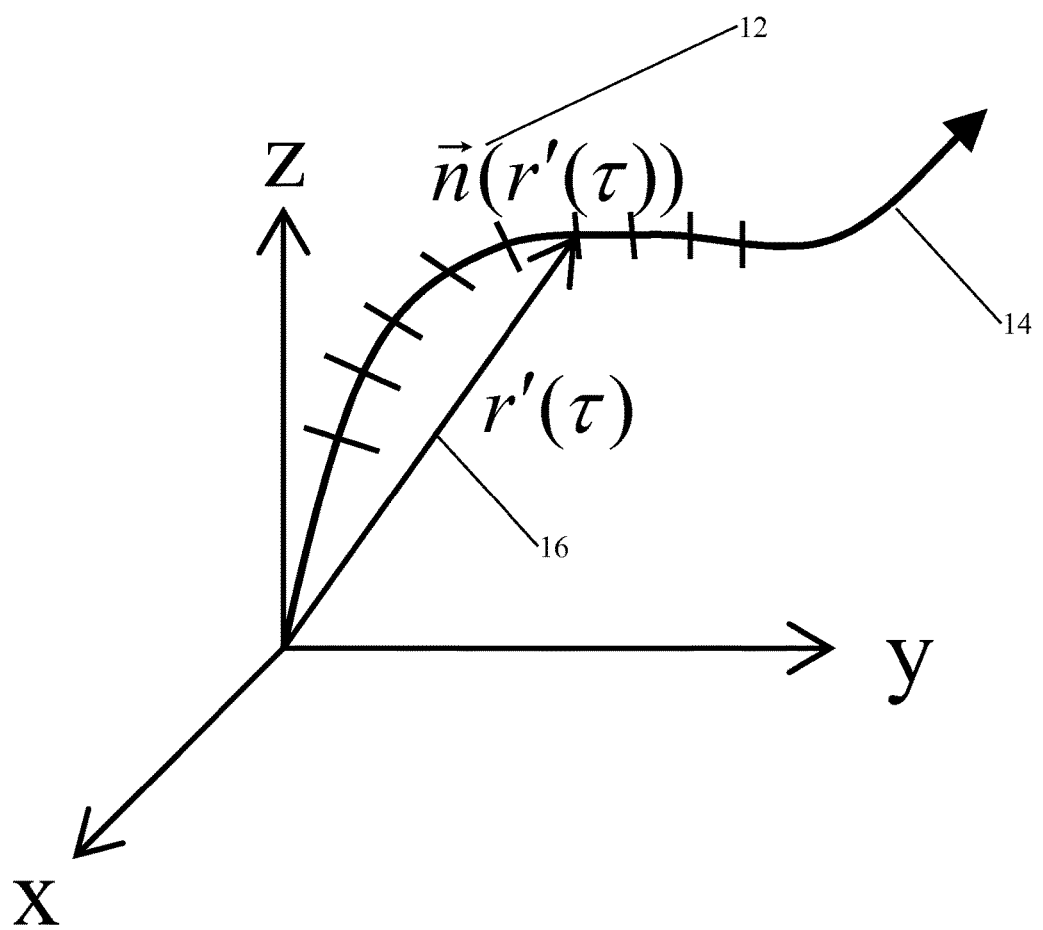
FIG. 2 is a general right handed orthogonal coordinate system showing the local position of a typical fiber pathway as well as a local tangent vector along the pathway.

Referring now to FIG. 2, the spatial-spectral filter is a method for separating, out of a complicated wave field, only those displacement components which are propagating along specific directions at every individual location along pathway 14 within a region of interrogation (ROI) comprised of a specific wavenumber spectrum. When a wave vector k depends on unit vectors 12 at each location as $k=kn_i(r')$, (i=1,3) and k is a scalar, the following spatial-spectral filter representation of $u_{SF}(r')$ holds:

$$U(kn_i(r')) = \int dr u(r) e^{-ikn_i(r') \cdot r} \quad [1]$$

$$u_{SF}(r') = \frac{1}{2\pi} \int_{I_k} dk e^{ikn_i(r') \cdot r'} U(kn_i(r')) \quad [2]$$

where $I_k$ represents the interval of variation of k=|k| and dependence on arclength, τ, is assumed. These expressions represent a spatial-spectral filter that provides the wave components that are traveling along specific directions relative to the path of a waveguide 14 defined by r' 16. Equations [1] and [2] are equivalent to a spatially dependent Radon transform. For the displacements within this local reference frame with spatially dependent components $n_1(r')$, $n_2(r')$, $n_3(r')$, of unit vector n(r') 12, and filtered representation as $u_{SF}(r')$ where r' is the local position vector, the following set of relationships holds:

$$u_1 = n_{1,x} u_{SF,x} + n_{1,y} u_{SF,y} + n_{1,z} u_{SF,z},$$

$$u_2 = n_{2,x} u_{SF,x} + n_{2,y} u_{SF,y} + n_{2,z} u_{SF,z},$$

$$u_3 = n_{3,x} u_{SF,x} + n_{3,y} u_{SF,y} + n_{3,z} u_{SF,z}, \quad [3]$$

The Helmholtz decomposition provides a method for separating a complicated wavefield into longitudinal (compressional) and transverse (shear) components. This is performed such that pure modes of propagation can be used in the inversions. The total displacement can be expressed as the sum of three components such that $$u(r) = u_L(r) + u_T(r) + u_H(r), \quad [4]$$

where $u_L(r)$ is the longitudinal (or irrotational) component and $u_T(r)$ is the transverse (or solenoidal) component and $u_H(r)$ is the Hodge term. This nomenclature is related to the following conditions imposed on the three components:

$$\nabla \cdot u = \nabla \cdot u_L \text{ and } \nabla \times u_L = 0.$$

$$\nabla \times u = \nabla \times u_T \text{ and } \nabla \cdot u_T = 0.$$

$$\nabla \cdot u_H = 0 \text{ and } \nabla \times u_H = 0. \quad [5]$$

The spatial Fourier transforms of these vectors can be shown to be:

$$U_L(k) = -\frac{k(U(k) \cdot k)}{k^2},$$

$$U_T(k) = -\frac{k \times (U(k) \times k)}{k^2}. \quad [6]$$

There are two methods to evaluate the Laplacians along the pathways: one includes the effects of curvature on the wave propagation, and the other assumes plane wave propagation along the local tangent vectors free from the effects of curvature. The representation of the Laplacian which includes the effects of curvature on the wave propagation can be obtained by differentiating Equations 3 twice with respect to arc length to obtain the following expressions where dependence on j=1,3 (x,y,z) is assumed:

$$\frac{\partial^2 \hat{u}_i(r'(\tau))_i}{\partial \tau^2} = \hat{n}_j(r'(\tau)) \cdot \frac{\partial^2 u_{SF_i}(r'(\tau))}{\partial \tau^2} + \quad [7]$$
$$2 \frac{\partial \hat{n}_j(r'(\tau))}{\partial \tau} \cdot \frac{\partial u_{SF_i}(r'(\tau))}{\partial \tau} + \frac{\partial^2 \hat{n}_j(r'(\tau))}{\partial \tau^2} \cdot u_{SF_i}(r'(\tau)),$$

where

-continued $$\frac{\partial u_{SF_i}(r'(\tau))}{\partial \tau} = \quad [8]$$
$$\frac{1}{2\pi}\int_{I_k} \frac{\partial U(kn_i(r'(\tau)))}{\partial \tau} e^{ikn_i(r'(\tau)) \cdot r'(\tau)} dk + \frac{1}{2\pi}\int_{I_k} U(kn_i(r'(\tau)))$$
$$ik\left[n_i(r'(\tau)) \cdot \frac{\partial r'(\tau)}{\partial \tau} + \frac{\partial n_i(r'(\tau))}{\partial \tau} \cdot r'(\tau)\right] e^{ikn_i(r'(\tau)) \cdot r'(\tau)} dk,$$

$$\frac{\partial^2 u_{SF_i}(r'(\tau))}{\partial \tau^2} = \quad [9]$$
$$\frac{1}{2\pi}\int_{I_k} \frac{\partial^2 U(kn_i(r'(\tau)))}{\partial \tau^2} e^{ikn_i(r'(\tau)) \cdot r'(\tau)} dk + \frac{2}{2\pi}\int_{I_k} \frac{\partial U(kn_i(r'(\tau)))}{\partial \tau}$$
$$ik\left[n_i(r'(\tau)) \cdot \frac{\partial r'(\tau)}{\partial \tau} + \frac{\partial n_i(r'(\tau))}{\partial \tau} \cdot r'(\tau)\right] e^{ikn_i(r'(\tau)) \cdot r'(\tau)} dk +$$
$$\frac{1}{2\pi}\int_{I_k} U(kn_i(r'(\tau)))ik\left[n_i(r'(\tau)) \cdot \frac{\partial^2 r'(\tau)}{\partial \tau^2} + 2\frac{\partial n_i(r'(\tau))}{\partial \tau} \cdot \frac{\partial r'(\tau)}{\partial \tau} + \right.$$
$$\left. \frac{\partial^2 n_i(r'(\tau))}{\partial \tau^2} \cdot r'(\tau)\right] e^{ikn_i(r'(\tau)) \cdot r'(\tau)} dk +$$
$$\frac{1}{2\pi}\int_{I_k} U(kn_i(r'(\tau)))(-k^2)\left[n_i(r'(\tau)) \cdot \frac{\partial r'(\tau)}{\partial \tau} + \frac{\partial n_i(r'(\tau))}{\partial \tau} \cdot r'(\tau)\right]^2$$
$$e^{ikn_i(r'(\tau)) \cdot r'(\tau)} dk,$$

$$\frac{\partial U(kn_i(r'(\tau)))}{\partial \tau} = \int_\Omega u(r)\left(-ik\frac{\partial n_i(r'(\tau))}{\partial \tau} \cdot r\right) e^{-ikn_i(r'(\tau)) \cdot r} dr, \quad [10]$$

and $$\frac{\partial^2 U(kn_i(r'(\tau)))}{\partial \tau^2} = \int_\Omega u(r)\left[(-ik)\frac{\partial^2 n_i(r'(\tau))}{\partial \tau^2} \cdot r\right] e^{-ik_i(r'(\tau)) \cdot r} dr +$$
$$\int_\Omega u(r)(-k^2)\left[\frac{\partial n_i(r'(\tau))}{\partial \tau} \cdot r\right]^2 e^{-ikn_i(r'(\tau)) \cdot r} dr.$$

The representation free from the effects of curvature can be identified as being the first term in Equation [7] and the term in the fourth line of Equation [9]. This assumes plane wave propagation along the local tangent vector alone. The effects of including curvature can be seen to bias the "inherent" material parameter as an index of refraction alters wave speed in ray theory. Therefore, the orthotropic inversion can be computed at each pixel free from the effects of curvature providing the nine "inherent" viscoelastic coefficients.

Referring now to FIG. 3, orthotropic elastic tensor 11 (also referred to as the stiffness tensor) of the white matter that is computed subject to monochromatic excitation is shown. Orthotropic elastic tensor 11 includes nine independent coefficients—six diagonal coefficients—$C_{11}$, $C_{22}$, $C_{33}$, $C_{44}$, $C_{55}$, $C_{66}$—and three off-diagonal coefficients—$C_{12}$, $C_{13}$, $C_{23}$.

Figure 4:
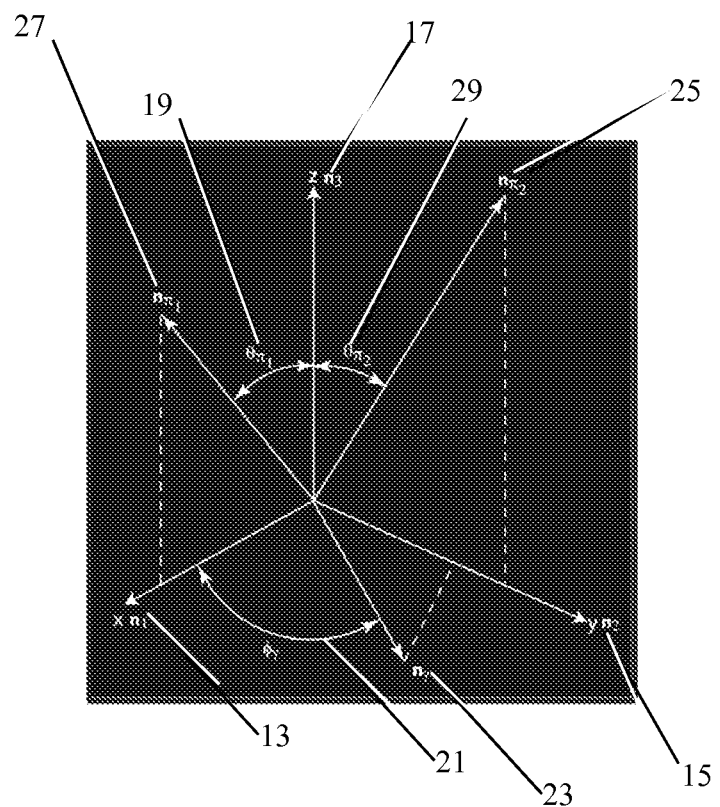
FIG. 4 is a graphical depiction of the local coordinate system showing the three major orthogonal axes as well as the three planes for pure longitudinal wave propagation.

Referring now to FIG. 4, for plane wave propagation along the pathways free from the effects of curvature, the diagonal of the orthotropic elastic tensor subject to monochromatic excitation, the following relationships hold:

Along $n_1(r)$ 13, $$C_{11}\frac{\partial^2 u_1^L(n_1)}{\partial x_1^2} = -\rho\omega^2 u_1^L(n_1) \quad [11a]$$

$$C_{66}\frac{\partial^2 u_2^T(n_1)}{\partial x_1^2} = -\rho\omega^2 u_2^T(n_1) \quad [11b]$$

$$C_{55}\frac{\partial^2 u_3^T(n_1)}{\partial x_1^2} = -\rho\omega^2 u_3^T(n_1) \quad [11c]$$

Along $n_2(r)$ 15, $$C_{66}\frac{\partial^2 u_1^T(n_2)}{\partial x_2^2} = -\rho\omega^2 u_1^T(n_2) \quad [12a]$$

$$C_{22}\frac{\partial^2 u_2^L(n_2)}{\partial x_2^2} = -\rho\omega^2 u_2^L(n_2) \quad [12b]$$

$$C_{44}\frac{\partial^2 u_3^T(n_2)}{\partial x_2^2} = -\rho\omega^2 u_3^T(n_2) \quad [12c]$$

Along $n_3(r)$ 17, $$C_{55}\frac{\partial^2 u_1^T(n_3)}{\partial x_3^2} = -\rho\omega^2 u_1^T(n_3) \quad [13a]$$

$$C_{44}\frac{\partial^2 u_2^T(n_3)}{\partial x_3^2} = -\rho\omega^2 u_2^T(n_3) \quad [13b]$$

$$C_{33}\frac{\partial^2 u_3^L(n_3)}{\partial x_3^2} = -\rho\omega^2 u_3^L(n_3) \quad [13c]$$

Referring again primarily to FIG. 4, method 150 (FIG. 1) is applied along a central fiber within the CSTs of each subject with the local vertical orientation of the fiber defined as the $n_3$ (r') 17 direction. If each vector position of the central fiber is provided by DTI, the local reference frame can be evaluated and the spatial-spectral filter (Equations [1-2]) and the Helmholtz decomposition (Equations [4-6]) can be applied to the displacements over a volume of, for example, 16×16×30 pixels (x,y,z) about the fiber to provide the filtered displacements at each data point using a Cooley-Tukey wavenumber filter with window widths appropriate for the frequencies of excitation obtained from an analysis of the longitudinal and transverse wavenumber spectra in an attempt to isolate the dominant wave components for each wave type. The diagonal of the Orthotropic tensor can then be solved using Equations [11a-c], [12a-c], and [13a-c]).

Continuing to refer to FIG. 4, for the three specific pure longitudinal mode directions, the unit vector $n_\gamma$ 23 is defined as being the propagation direction that lies within the x-y plane ($n_1$ 13-$n_2$ 15 plane), at an angle $\varphi_\gamma$ 21 referenced from the x ($n_1$) 13 axis. Correspondingly, $n_{\pi_1}$ 27 is the propagation direction which lies within the x-z plane ($n_1$-$n_3$ plane), at an angle $\theta_{\pi_1}$ 19 referenced from the z ($n_3$) 17 axis. Finally, $n_{\pi_2}$ 25 is the propagation direction which lies within the y-z plane ($n_2$-$n_3$ plane), at an angle $\theta_{\pi_2}$ 29 referenced from the z($n_3$) 17 axis. With these definitions, the following relationships for the equations of motion within these planes hold:

Along $n_\gamma(r)$ 23, $$C_{11}\frac{\partial^2 u_1^L(n_\gamma)}{\partial x_1^2} + C_{66}\frac{\partial^2 u_1^L(n_\gamma)}{\partial x_2^2} + (C_{12}+C_{66})\frac{\partial^2 u_2^L(n_\gamma)}{\partial x_1 \partial x_2} = \quad [14a]$$
$$-\rho\omega^2 u_1^L(n_\gamma)$$

$$(C_{12}+C_{66})\frac{\partial^2 u_1^L(n_\gamma)}{\partial x_1 \partial x_2} + C_{66}\frac{\partial^2 u_2^L(n_\gamma)}{\partial x_1^2} + C_{22}\frac{\partial^2 u_2^L(n_\gamma)}{\partial x_2^2} = -\rho\omega^2 u_2^L(n_\gamma) \quad [14b]$$

Along $n_{\pi_2}(r)$ 25, $$C_{22}\frac{\partial^2 u_2^L(n_{\pi_2})}{\partial x_2^2} + C_{44}\frac{\partial^2 u_2^L(n_{\pi_2})}{\partial x_3^2} + (C_{44}+C_{23})\frac{\partial^2 u_3^L(n_{\pi_2})}{\partial x_2 \partial x_3} = \quad [15a]$$
$$-\rho\omega^2 u_2^L(n_{\pi_2})$$

$$(C_{44}+C_{23})\frac{\partial^2 u_2^L(n_{\pi_2})}{\partial x_2 \partial x_3}+C_{44}\frac{\partial^2 u_3^L(n_{\pi_2})}{\partial x_2^2}+C_{33}\frac{\partial^2 u_3^L(n_{\pi_2})}{\partial x_3^2}= \quad [15b]$$
$$-\rho\omega^2 u_3^L(n_{\pi_2})$$

Along $n_{\pi_1}(r)$ 27, [16a]

$$C_{11}\frac{\partial^2 u_1^L(n_{\pi_1})}{\partial x_1^2}+C_{55}\frac{\partial^2 u_1^L(n_{\pi_1})}{\partial x_3^2}+(C_{13}+C_{55})\frac{\partial^2 u_3^L(n_{\pi_1})}{\partial x_1 \partial x_3}=$$
$$-\rho\omega^2 u_1^L(n_{\pi_1})$$

$$(C_{13}+C_{55})\frac{\partial^2 u_1^L(n_{\pi_1})}{\partial x_1 \partial x_3}+C_{55}\frac{\partial^2 u_3^L(n_{\pi_1})}{\partial x_1^2}+C_{33}\frac{\partial^2 u_3^L(n_{\pi_1})}{\partial x_3^2}= \quad [16b]$$
$$-\rho\omega^2 u_3^L(n_{\pi_1})$$

In Equations [11-16], $u_1$ ($n_1$), $u_2$ ($n_2$), $u_3$ ($n_3$), $u_\gamma$ ($n_\gamma$), $u_{\pi_1}$ ($n_{\pi_1}$), and $u_{\pi_2}$ ($n_{\pi_2}$) represent the directionally filtered displacements provided by the spatial-spectral filter and a temporal Fourier transform. $x_1$, $x_2$, and $x_3$, are the differential parameters along the local axes, and the superscripts L and T correspond to the longitudinal and transverse components provided by the Helmholtz decomposition; dependence on r' is assumed. Equations [11a-c], [12a-c], and [13a-c] are solved by a simple division of the right hand side by the 1-D Laplacians for a solution of the complex elastic coefficients for $C_{11}$, $C_{22}$, $C_{33}$, $C_{44}$, $C_{55}$, and $C_{66}$. These values for the coefficients are then inserted into Equations [14a-b], [15a-b], and [16a-b] as known values, and solutions for the remaining complex coefficients $C_{12}$, $C_{23}$, and $C_{13}$ are solved for simultaneously within each separate plane by rotating the angles of interrogation, $\varphi_\gamma$ 21, $\theta_{\pi_1}$ 19, and $\theta_{\pi_2}$ 29 (FIG. 4) to minimize the Euclidian distance between the complex solutions of each pair of equations (Equations [14a-b], [15a-b], and [16a-b], respectively) thereby also providing these longitudinal propagation angles.

Complex elastic coefficients $C_{11}$-$C_{66}$ (FIG. 3) can be used to compute the corresponding velocity (V) and attenuation ($\alpha$) along the specific directions through the following relationships:

$$V(\omega)\frac{1}{Re\left[\sqrt{\frac{\rho}{C_{jj}(\omega)}}\right]} \quad [17]$$

$$\alpha(\omega)=\omega \, Im\left[\sqrt{\frac{\rho}{C_{jj}(\omega)}}\right] \quad [18]$$

where j=1,6. More general relationships for anisotropic wave velocities are possible.

Redundancies in the coefficients of the orthotropic elastic tensor can expose lower order anisotropic (or isotropic) models as being valid or representative of the medium. For example, while the orthotropic elastic tensor includes nine independent elastic coefficients, redundancies in the solution for these coefficients indicated that the corticospinal tracts (CSTs) could be well represented by a hexagonal (transversely isotropic) model comprised of five independent elastic coefficients. In this fashion, the method of the present embodiment can be adapted to an unknown medium being evaluated. The orthotropic elastic tensor, including nine elastic coefficients, is the highest order anisotropic model that can be used to solve for the individual coefficients separately of one another avoiding ill conditionedness in the inversion procedure. Few materials in nature have a higher degree of anisotropy than orthotropy. Thus, with the model described above, there is a reasonable approximation of the degree of anisotropy either characteristic of, or exceeding that of human tissue.

Continuing to refer to FIG. 4, a local reference frame can be calculated based on a plane perpendicular to the elastic wave pathways. The evaluation of a consistent local right handed coordinate system—a local reference frame—is essential to interpret the inversion results in anisotropic media as they curve and twist. The vectors n1, n2, and n3 can rotate, so a stable formulation must be included to evaluate them and provide the dot-product projection of the filtered displacements ($u_{sf}$) with these rotating coordinate vectors. If $n_3$ is the local tangent vector along the principal fiber pathway, n1 and n2 can be evaluated as follows.

The point normal representation of a plane with normal $\vec{n}_3$ can be expressed as.

$$n_{3x}(x-x_0)+n_{3y}(y-y_0)+n_{3z}(z-z_0)=0 \quad (19)$$

For a solution for $\vec{n}_2$ which lies in this plane and is perpendicular to $\vec{n}_3$, let $n_{2y}=n_{3z}$. Then, $n_{2y}=y-y_0$, and therefore $y=n_{2y}+y_0=n_{3z}+y_0$. Now, $$\vec{n}_3\cdot\vec{n}_2=n_{3x}\cdot n_{2x}+n_{3y}\cdot n_{2y}+n_{3z}\cdot n_{2z}=0, \quad (20)$$

$n_{2y}=n_{3z}$, and $n_{2x}=n_{3y}$. Thus, $$n_{3x}\cdot n_{3y}+n_{3y}\cdot n_{3z}+n_{3z}\cdot n_{2z}=0. \quad (21)$$

Solving for $n_{2z}$, we have $$n_{2z}=-\frac{(n_{3x}\cdot n_{3y}+n_{3y}\cdot n_{3z})}{n_{3z}}, \quad (22)$$

$n_{3z}\neq 0$. Since $\vec{n}_2$ lies in the plane provided by $\vec{n}_3$, $$\vec{n}_1=\vec{n}_2\times\vec{n}_3, \quad (23)$$

which also lies in the plane. More general representations may be easily developed.

Figure 5:
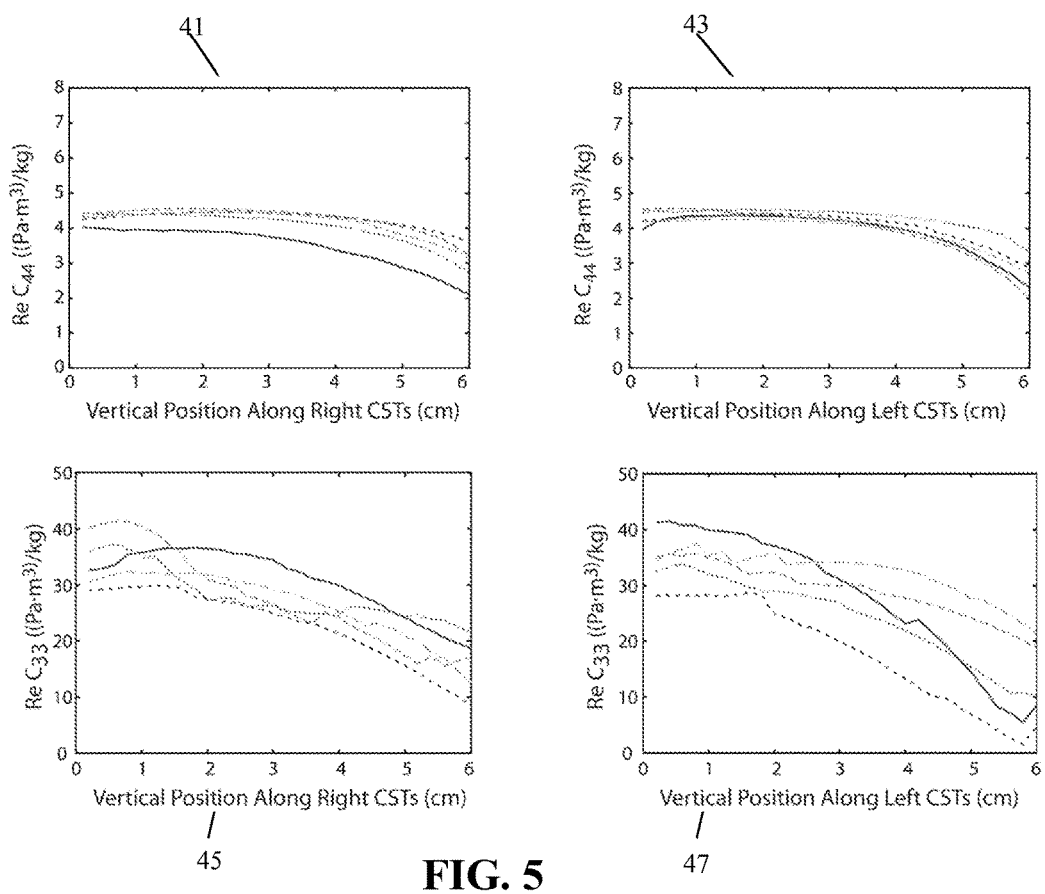
FIG. 5 is an example of the application of the system and method of the present embodiment to the evaluation of the stiffness coefficients C33 and C44 in the CSTs of five healthy volunteers.

Referring now to FIG. 5, the results of a practical application of the system and method of the present embodiment using two FDA-approved clinical measurement modalities, MRE and DTI, using a standard 1.5 Tesla MRI scanner is shown. Graphs 41-47 portray typical stiffness profiles for the shear and longitudinal coefficients C44 and C33, respectively, along the right and left CSTs for five healthy volunteers.

Figure 6:
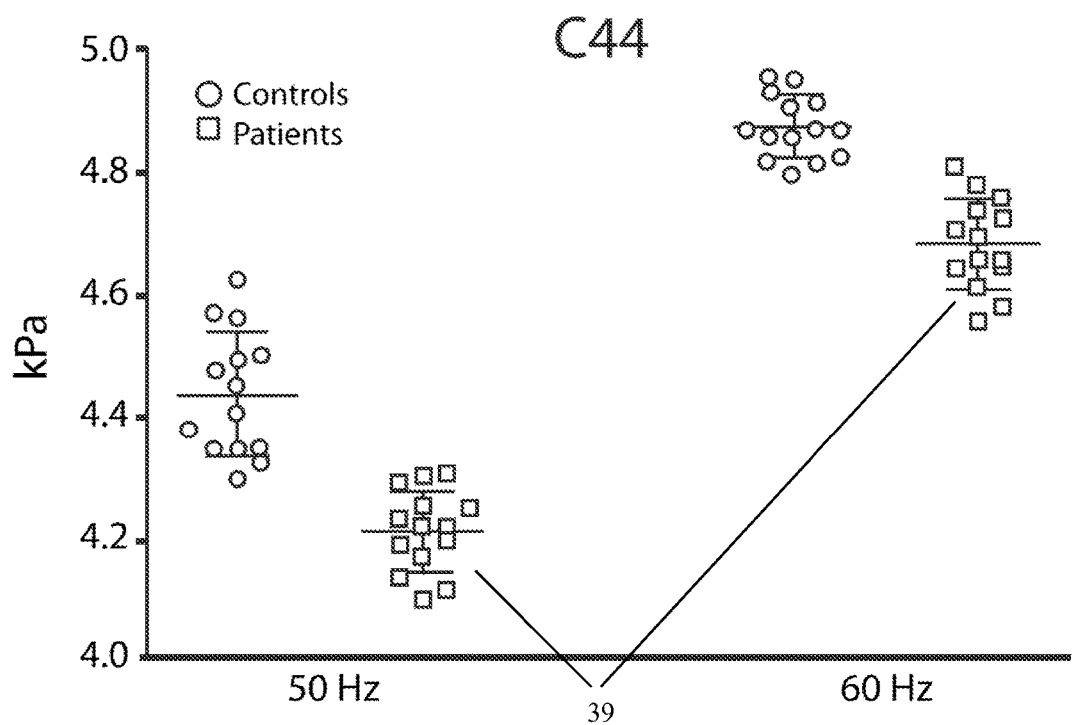
FIG. 6 is a graphical depiction of an application of the system and method of the present embodiment to the detection of Amyotrophic Lateral Sclerosis in 28 volunteers.

Referring now to FIG. 6, twenty-eight volunteers (14 who were diagnosed with ALS and 14 healthy, age-matched controls) were scanned using MRE and DTI, and the results were processed using the system and method of the present embodiment. Study data were initially blinded. Patients clustered into four distinct groups with ALS patients 39 clustered together correctly.

Figure 7:
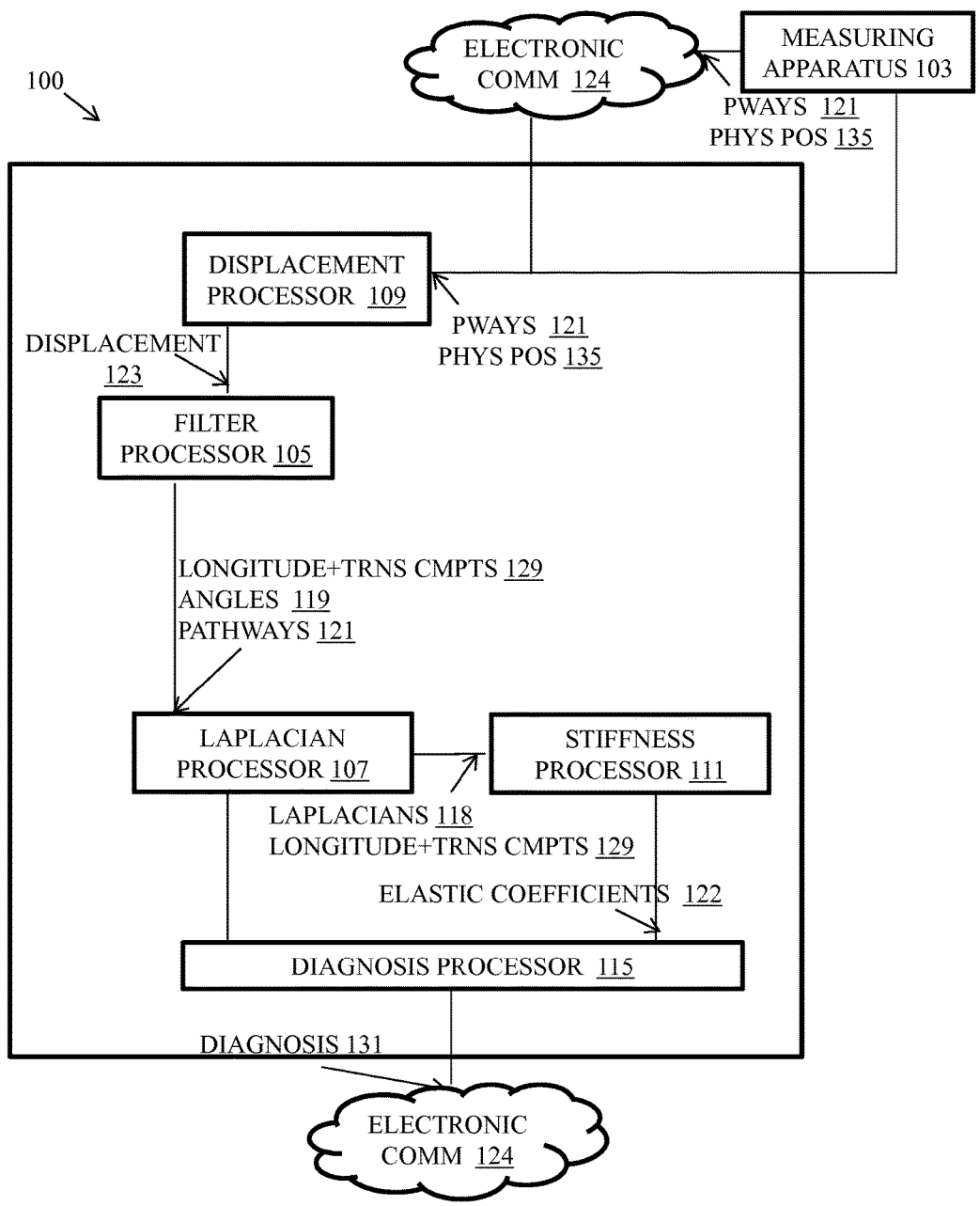
FIG. 7 is a schematic block diagram of the system of the present embodiment.

Referring now to FIG. 7, system 100 for diagnosing a brain condition can include, but is not limited to including, measuring apparatus 103 measuring a physical position 135 in space relative to a global coordinate system of fiber pathways 121 within an anisotropic medium, System 100 can also include displacement processor 109 measuring dynamic elastic displacements 123 within a volume surrounding fiber pathways 121 at locations of measured physical position 135, and filter processor 105 applying a spatial-spectral filter to measured displacements 123 to obtain elastic wave components traveling at angles 119 to and along fiber pathways 121, filter processor 105 applying a Helmholtz decomposition to the filtered displacements to determine longitudinal and transverse components 129. System 100 can still further include Laplacian processor 107 computing Laplacians 118 by differentiating longitudinal and transverse components 129 twice with respect to arc length along angles 119 and along fiber pathways 121, stiffness processor 111 evaluating elastic coefficients 122 by dividing the acceleration of longitudinal and transverse components 129 by Laplacians 118 corresponding to longitudinal and transverse components 129, and diagnosis processor 115 diagnosing the brain condition 131 based on elastic coefficients 122 identified along the pathways 121.

Filter processor 105 can optionally include applying a global band-limited filter before applying the spatial-spectral filter, and applying a sliding window band-limited filter based on the longitudinal and transverse components. Laplacian processor 107 can optionally include calculating a local reference frame based on the global coordinate system and on a plane perpendicular to the pathways, and extending the pathways using automated tractography. The inversion can optionally be, but aren't limited to being, an orthotropic inversion, a monoclinic inversion, a triclinic inversion, a cubic inversion, a hexagonal inversion, a trigonal inversion, an isotropic inversion, or a tetragonal inversion.

Embodiments of the present teachings are directed to computer systems such as system 100 (FIG. 7) for accomplishing the methods such as method 150 (FIG. 1) discussed in the description herein, and to computer readable media containing programs for accomplishing these methods. The raw data and results can be stored for future retrieval and processing, printed, displayed, transferred to another computer, and/or transferred elsewhere. Communications links such as electronic communications 124 (FIG. 7) can be wired or wireless, for example, using cellular communication systems, military communications systems, and satellite communications systems. In an exemplary embodiment, the software for the system is written in FORTRAN, C, or MATLAB®. The system can operate on a computer having a variable number of CPUs. Other alternative computer platforms can be used. The operating system can be, for example, but is not limited to, LINUX®.

The present embodiment is also directed to software for accomplishing the methods discussed herein, and computer readable media storing software for accomplishing these methods. The various modules described herein can be accomplished on the same CPU, or can be accomplished on different computers. In compliance with the statute, the present embodiment has been described in language more or less specific as to structural and methodical features. It is to be understood, however, that the present embodiment is not limited to the specific features shown and described, since the means herein disclosed comprise preferred forms of putting the present embodiment into effect.

Methods such as method 150 (FIG. 1) of the present embodiment can be, in whole or in part, implemented electronically. Signals representing actions taken by elements of the system and other disclosed embodiments can travel over at least one live communications network 124 (FIG. 7). Control and data information can be electronically executed and stored on at least one computer-readable medium. System 100 (FIG. 7) can be implemented to execute on at least one computer node in at least one live communications network 124 (FIG. 7). Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form including, but not limited to, Graphic Interchange Format (GIF), Joint Photographic Experts Group (JPEG), Portable Network Graphics (PNG), Scalable Vector Graphics (SVG), and Tagged Image File Format (TIFF).

Although the present teachings have been described with respect to various embodiments, it should be realized these teachings are also capable of a wide variety of further and other embodiments.

What is claimed is:

1. A noninvasive computer-based method for diagnosing a brain condition, the method comprising:
   measuring, using a processing device, a physical position in space relative to a global coordinate system of fiber pathways within an anisotropic medium;
   measuring, using the processing device, dynamic elastic displacements within a volume surrounding the fiber pathways at locations of the measured physical position;
   applying, using the processing device, a spatial-spectral filter to the measured displacements to obtain elastic wave components traveling at angles to and along the fiber pathways;
   applying, using the processing device, a Helmholtz decomposition to the filtered displacements to determine longitudinal and transverse components;
   computing, using the processing device, Laplacians corresponding to the elastic wave components by differentiating the longitudinal and transverse components twice with respect to a parameterized representation of the fiber pathways along the angles and along the fiber pathways, wherein the Laplacians correspond to the elastic wave components and include effects of curvature on stiffness along the fiber pathways, wherein the effects of curvature include derivatives of a parameterized position vector of the spatial spectral filter;
   evaluating, using the processing device, elastic coefficients by dividing an acceleration of the longitudinal and transverse components by the Laplacians corresponding to the longitudinal and transverse components; and
   diagnosing, using the processing device, the brain condition based on the elastic coefficients identified along the fiber pathways.

2. The method as in claim 1, further comprising:
   applying a global band-limited filter to the measured displacements before applying the spatial-spectral filter.

3. The method as in claim 1, further comprising:
   calculating a local reference frame based on the global coordinate system and on a plane perpendicular to the fiber pathways.

4. The method as in claim 1, further comprising:
   extending the fiber pathways using automated tractography.

5. The method of claim 1, wherein measuring the dynamic elastic displacements further comprises:
   measuring the dynamic elastic displacements using a Magnetic Resonance Elastography (MRE) process.

6. The method of claim 5, further comprising:
determining the fiber pathways using a diffusion tensor imaging (DTI) process.

7. The method of claim 6, wherein the spatial-spectral filter obtains the elastic wave components based on results from both the MRE process and the DTI process.

8. The method of claim 6, further comprising:
computing the Laplacians based on results from both the MRE process and the DTI process.

9. The method of claim 1, wherein the effects of curvature are nonlinear.

10. The method of claim 1, further comprising:
determining an inversion model for the fiber pathways based on an output of the spatial-spectral filter and an output of the Helmholtz decomposition.

11. The method of claim 10, wherein the inversion model is an orthotropic inversion model.

12. The method of claim 10, wherein the inversion model is a monoclinic inversion model.

13. The method of claim 10, wherein the inversion model is a triclinic inversion model.

14. The method of claim 10, wherein the inversion model is a hexagonal inversion model.

15. The method of claim 10, wherein the inversion model is a trigonal inversion model.

16. A noninvasive computer-based method for diagnosis of brain conditions, the method comprising:
determining fiber pathways of white matter tracts using a diffusion tensor imaging (DTI) process, the white matter tracts having viscoelastic properties, the DTI process having a specific spatial resolution and a voxel position;
measuring elastic waves traveling within a volume surrounding the fiber pathways by performing a 3D magnetic resonance elastography (MRE) process at the same spatial resolution and voxel position as the DTI process;
identifying the elastic waves traveling at pre-selected angles with respect to the white matter tracts using a spatial-spectral filter on the measured elastic waves;
evaluating longitudinal and transverse components of the identified elastic waves using a Helmholtz decomposition;
determining a parameterized representation of Laplacians of the identified elastic waves, wherein the parameterized representation is $\partial^2 u_{SF}(r'(\tau))/\partial \tau^2$, wherein $u_{SF}$ represents a spatial spectral filter of the measured displacements, and wherein $r'(\tau)$ represents a parameterized position vector along the fiber pathways;
evaluating Laplacians of the identified elastic waves based on the parameterized representation, wherein the Lapiacians include effects of curvature on stiffness along the fiber pathways, and wherein the effects of curvature include derivatives of the parameterized position vector;
dividing an acceleration of the longitudinal and transverse components by Laplacians corresponding to the longitudinal and transverse components to obtain viscoelastic coefficients; and
diagnosing the brain conditions based on the viscoelastic coefficients.

17. A system for diagnosing a brain condition, the system comprising:
a measuring device configured to measure a physical position in space relative to a global coordinate system of fiber pathways within an anisotropic medium;
a displacement processor configured to measure dynamic elastic displacements within a volume surrounding the fiber pathways at locations of the measured physical position;
a filter processor configured to apply a spatial-spectral filter to the measured displacements to obtain elastic wave components traveling at angles to and along the fiber pathways, the filter processor applying a Helmholtz decomposition to the filtered displacements to determine longitudinal and transverse components;
a Laplacian processor configured to compute Laplacians corresponding to the elastic wave components by differentiating the longitudinal and transverse components twice with respect to a parameterized representation of the fiber pathways along the angles and along the fiber pathways, wherein the Laplacians correspond to the elastic wave components and include effects of curvature on stiffness along the fiber pathways, wherein the effects of curvature include derivatives of a parameterized position vector of the spatial spectral filter;
a stiffness processor configured to evaluate elastic coefficients by dividing an acceleration of the longitudinal and transverse components by the Laplacians corresponding to the longitudinal and transverse components; and
a diagnosis processor configured to diagnose the brain condition based on the elastic coefficients identified along the fiber pathways.

18. The system as in claim 17, wherein the filter processor is further configured to:
apply a global band-limited filter to the measured displacements before applying the spatial-spectral filter.

19. The system as in claim 17, wherein the Laplacian processor further comprises:
calculating a local reference frame based on the global coordinate system and on a plane perpendicular to the fiber pathways.

20. The system as in claim 17, wherein the Laplacian processor further comprises:
extending the fiber pathways using automated tractography.

* * * * *